US008778392B2

(12) United States Patent
Matsuoka et al.

(10) Patent No.: US 8,778,392 B2
(45) Date of Patent: Jul. 15, 2014

(54) ORAL DISINTEGRATING TABLET

(75) Inventors: Makoto Matsuoka, Ibaraki (JP);
Hiroyuki Nishii, Ibaraki (JP); Maki Kawamura, Ibaraki (JP)

(73) Assignee: Dainippon Sumitomo Pharma Co., Ltd., Osaka-shi (JP)

(*) Notice: Subject to any disclaimer, the term of this patent is extended or adjusted under 35 U.S.C. 154(b) by 175 days.

(21) Appl. No.: 12/531,150

(22) PCT Filed: Mar. 12, 2008

(86) PCT No.: PCT/JP2008/054529
§ 371 (c)(1),
(2), (4) Date: Sep. 14, 2009

(87) PCT Pub. No.: WO2008/120548
PCT Pub. Date: Oct. 9, 2008

(65) Prior Publication Data
US 2010/0098756 A1 Apr. 22, 2010

(30) Foreign Application Priority Data
Mar. 13, 2007 (JP) ................................. 2007-063913

(51) Int. Cl.
*A61K 9/20* (2006.01)
*A61K 31/4422* (2006.01)
*A61K 9/12* (2006.01)
*A61K 31/519* (2006.01)
*A61K 31/47* (2006.01)

(52) U.S. Cl.
USPC ........... 424/464; 424/465; 514/424; 514/353; 514/379

(58) Field of Classification Search
USPC ........ 424/464, 465; 514/424, 353, 239.9, 379
See application file for complete search history.

(56) References Cited

U.S. PATENT DOCUMENTS

| 5,466,464 | A | 11/1995 | Masaki et al. |
| 5,529,789 | A | 6/1996 | Lo |
| 5,837,285 | A | 11/1998 | Nakamichi et al. |
| 5,958,453 | A | 9/1999 | Ohno et al. |
| 6,106,861 | A | 8/2000 | Chauveau et al. |
| 6,235,947 | B1 | 5/2001 | Yoshinari et al. |
| 6,248,357 | B1 | 6/2001 | Ohno et al. |
| 6,740,339 | B1 | 5/2004 | Ohkouchi et al. |
| 7,067,149 | B1 | 6/2006 | Chauveau et al. |
| 2001/0001106 | A1 | 5/2001 | Yoshinari et al. |
| 2001/0014340 | A1 | 8/2001 | Ohta et al. |
| 2002/0107420 | A1 | 8/2002 | Yoshinari et al. |
| 2003/0026835 | A1 | 2/2003 | Nishii et al. |
| 2003/0215500 | A1 | 11/2003 | Ohta et al. |
| 2004/0033258 | A1 | 2/2004 | Koike |
| 2004/0122106 | A1 | 6/2004 | Ohta et al. |
| 2004/0162333 | A1 | 8/2004 | Mezaache et al. |
| 2004/0180085 | A1 | 9/2004 | Ohkouchi et al. |
| 2005/0147666 | A1* | 7/2005 | Ohta et al. ............... 424/464 |
| 2005/0238712 | A1* | 10/2005 | Ohkouchi et al. ........ 424/464 |
| 2006/0115529 | A1 | 6/2006 | Jeong et al. |
| 2006/0134199 | A1 | 6/2006 | Suga et al. |
| 2006/0177508 | A1* | 8/2006 | Chauveau et al. ....... 424/469 |
| 2008/0095841 | A1* | 4/2008 | Suzuki et al. ........... 424/464 |
| 2008/0102133 | A1 | 5/2008 | Brueck-Scheffler et al. |
| 2008/0227849 | A1* | 9/2008 | Kano et al. .............. 514/424 |
| 2011/0053942 | A1* | 3/2011 | Fujiwara et al. ......... 514/239.5 |

FOREIGN PATENT DOCUMENTS

| CN | 1565425 A | 1/2005 |
| EP | 1 329 217 A1 | 7/2003 |
| EP | 1 366 759 A1 | 12/2003 |
| EP | 1 100 469 | 3/2005 |
| EP | 1 681 048 | 7/2006 |
| JP | 7-501829 | 2/1995 |
| JP | 9-71523 | 3/1997 |
| JP | 9-309821 | 12/1997 |
| JP | 9-309822 | 12/1997 |
| JP | 10-36291 | 2/1998 |
| JP | 10-182436 | 7/1998 |
| JP | 10-298062 | 11/1998 |
| JP | 11-35450 | 2/1999 |
| JP | 2000-273039 | 10/2000 |
| JP | 2001-58944 | 3/2001 |
| JP | 2001-122804 | 5/2001 |

(Continued)

OTHER PUBLICATIONS

Nippon Soda Co., Ltd Pharmaceutical Products Page. http://www.mmjp.or.jp/nisso-iyaku/hpc/hpc_english.html.*
Extended European Search Report issued Oct. 18, 2011, in Patent Application No. 08721945.7.
Office Action issued Aug. 24, 2011, in corresponding Russian Patent Application No. 2009137794/15(053422) (English translation).
Observations by Third Party in Japanese Patent Application No. 2009-507445 mailed Aug. 5, 2013 with English translation.
Iyakuhin Tenkabutsu Jiten 2000 (Japanese Pharmaceutical Excipients Directory 2000, Apr. 28, 2000, published by Yakuji Nippo Limited) with English translation.

(Continued)

Primary Examiner — Anoop Singh
Assistant Examiner — Anna Falkowitz
(74) Attorney, Agent, or Firm — Oblon, Spivak, McClelland, Maier & Neustadt, L.L.P.

(57) ABSTRACT

An oral disintegrating tablet containing (1) D-mannitol, (2) an active ingredient, (3) one or more disintegrating agents selected from the group consisting of crospovidone and carmellose, and (4) one or more lubricants selected from the group consisting of sodium stearyl fumarate and sucrose esters of fatty acids. The oral disintegrating tablet of the present invention has some excellent properties of (1) allowing easy production in a common facility without necessitating a specialized pharmaceutical technique, (2) having an appropriate strength that does not breakdown in the process of distribution, (3) having a fast disintegrating ability in the oral cavity, and (4) also having excellent ingestion feel such as greatly reduced bitterness or gritty feel; therefore, the tablet can be suitably used as a dosage form that is suitable for aged individuals, children, and seriously ill patients.

21 Claims, 1 Drawing Sheet

(56) References Cited

FOREIGN PATENT DOCUMENTS

| | | | | |
|---|---|---|---|---|
| JP | 2001-163770 | | 6/2001 | |
| JP | 2002-179558 | | 6/2002 | |
| JP | 2002-529392 | | 9/2002 | |
| JP | 2002-326927 | | 11/2002 | |
| JP | 2003-34655 | | 2/2003 | |
| JP | 2003-192695 | | 7/2003 | |
| JP | 2004-2326 | | 1/2004 | |
| JP | 2004-175796 | | 6/2004 | |
| JP | 2005-112861 | | 4/2005 | |
| JP | 2006-265242 | | 10/2006 | |
| JP | 2006-523620 | | 10/2006 | |
| WO | WO 93/12769 | | 7/1993 | |
| WO | WO97/47287 | | 12/1997 | |
| WO | WO00/47233 | | 8/2000 | |
| WO | WO 01/76565 A1 | | 10/2001 | |
| WO | WO 03/074085 A1 | | 9/2003 | |
| WO | WO 2004/064810 A1 | | 8/2004 | |
| WO | WO 2006/070705 | * | 12/2004 | .............. A61K 31/79 |
| WO | WO 2006/037763 A1 | | 4/2006 | |
| WO | WO 2006/038661 | * | 4/2006 | .............. A61K 9/16 |
| WO | WO 2006/070705 A1 | | 7/2006 | |
| WO | WO 2007/055427 | * | 5/2007 | .............. A61K 47/12 |

OTHER PUBLICATIONS

Daijirin (Japanese-Japanese Dictionary, First Printing Edition, Nov. 3, 1988, published by Sanseido Co., Ltd.) with English translation.

Observations by Third Party in Japanese Patent Application No. 2009-507445 mailed Aug. 22, 2013 with English translation.

Parteck, Functional Particle Engineering . . . For Optimal Performance, Advancing Your Life Sciences-From Discovery to Launch, Merck, pp. 1-7, with English translation.

Iyakuhin Tenkabutsu Jiten 2005 (Japanese Pharmaceutical Excipients Directory 2005, Jul. 12, 2005, p. 101, Published by Yakuji Nippo Limited) with English translation.

Iyakuhin Tenkabutsu Jiten 2005 (Japanese Pharmaceutical Excipients Directory 2005, Jul. 12, 2005, p. 189, published by Yakuji Nippo Limited) with English translation.

* cited by examiner

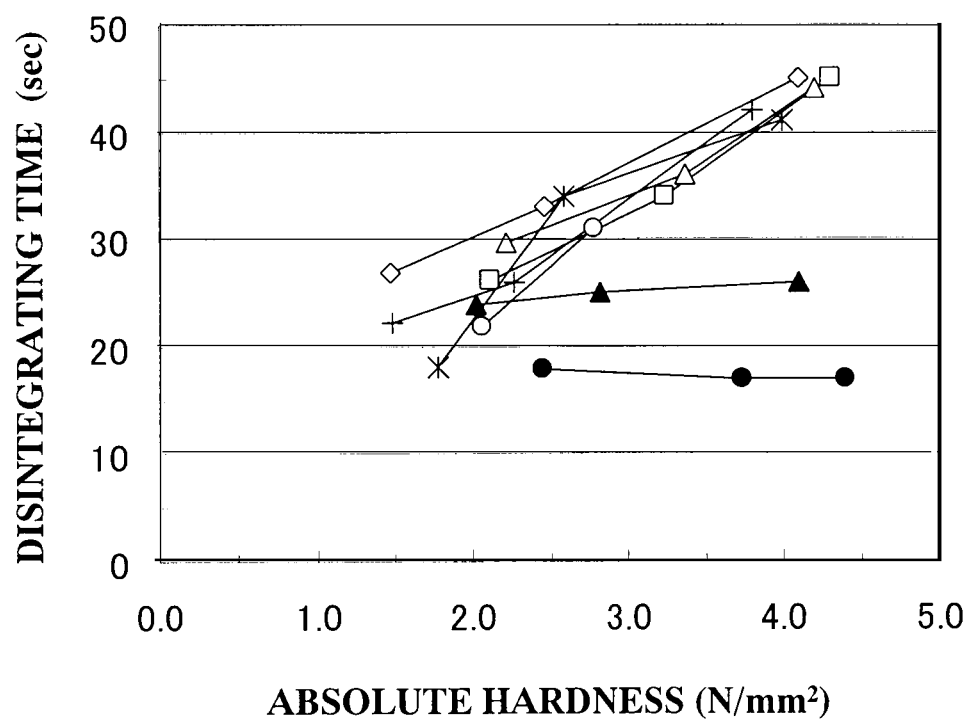

ORAL DISINTEGRATING TABLET

TECHNICAL FIELD

The present invention relates to a fast disintegrating tablet having fast disintegrating ability or dissolubility in the oral cavity, with a small amount of water or even without water.

BACKGROUND ART

Conventionally, various pharmaceutical dosage forms for oral administration are known. However, there are few dosage forms with consideration for easy ingestion for patients, and especially dosage forms that are suitable for aged individuals, children and seriously ill patients, who are likely to accompany difficulty in the ingestion of the dosage forms, are desired. For example, tablets and capsules are most commonly used dosage forms, from the viewpoint of its ability of dosing given amounts or physicochemical stability, and further from the viewpoint of production costs; on the other hand, many patients disfavor from ingesting the tablets and capsules, because of the reasons such as the tablets and capsules are less likely to be easily ingested, but caught at the throat. Powders and granules are more difficult to be swallowed, but remain in the oral cavity, thereby giving a lingering unpleasant after-taste in the mouth. Solutions such as syrups are considered to be dosage forms that are suitable for aged individuals and children; the ingestion of liquids by volumetric measurements accompanies difficulties for aged individuals, children and seriously ill patients, so that ingestion in an accurate amount cannot be expected. In addition, the liquids yet had some problems with physicochemical stability. In recent years, many techniques relating to formulations quickly disintegrating in the oral cavity are disclosed in the dosage forms having both maintenance of ability of dosing given amounts and physicochemical stability owned by the tablets and capsules and easy ingestion as in syrups (Patent Publications 1, 2, 3, and 4).

However, the above techniques have various problems in that a relatively large amount of water is used, so that the drug is more likely to be unstable, that the formulation does not have an appropriate strength so that there is a risk of being damaged in the process of distribution, and further that an impediment in tableting, such as sticking or capping, is caused upon tableting during the production process in tableting, thereby showing difficulty in handling the formulation.

Various combinations of additives and production methods have been studied in order to solve the above problems; however, a production method, for example, a method of drying tablets under humidification after molding, an external lubrication method, or the like is complicated, so that specialized apparatuses are necessitated in many cases.

Relatively commonly used techniques include those in Patent Publication 5, Patent Publication 6, and the like, and in any of these techniques, further studies must be made in order to provide an oral disintegrating tablet that shows fast disintegrating ability in the oral cavity and has an appropriate strength, and that does not dependent on a specialized production method.

Patent Publication 7 discloses a tablet not only showing a fast disintegrating ability and excellent feel upon ingestion in the oral cavity, but also having an appropriate strength so that the tablet does not breakdown in the process of distribution. In addition, Patent Publication 8 discloses a tablet that rapidly degrades (disintegrates) in the mouth, using a soluble diluent used in the form of a directly compressible formed product.

On the other hand, in the recent medical field work, even an oral disintegrating tablet is desired to have a high tablet strength, so that it is desired not only to prevent damages such as cracks and defects upon taking the tablet out from PTP (blister) packaging, but also to enable packaging by an automatic tablet packaging machine.

Patent Publication 1: Japanese Patent Laid-Open No. Hei 9-309821
Patent Publication 2: Japanese Patent Laid-Open No. Hei 9-309822
Patent Publication 3: WO 93/12769
Patent Publication 4: Japanese Unexamined Patent Publication No. Hei 7-501829
Patent Publication 5: Japanese Unexamined Patent Publication No. Hei 10-182436
Patent Publication 6: Japanese Patent Laid-Open No. Hei 9-71523
Patent Publication 7: WO 00/47233
Patent Publication 8: Japanese Patent Laid-Open No. Hei 11-35450

DISCLOSURE OF THE INVENTION

Problems to be Solved by the Invention

An object of the present invention is to provide an oral disintegrating tablet having excellent properties such as (1) allowing easy production in a common facility without requiring a specialized pharmaceutical technique, (2) having an appropriate strength so that the tablet is not damaged in the process of distribution, (3) having fast disintegrating ability in the oral cavity, and (4) also having excellent ingestion feel with greatly reduced bitterness or gritty feel.

Means to Solve the Problems

The present inventors have found that upon the preparation of an oral disintegrating tablet having the above-mentioned properties, a tablet disintegrating in the oral cavity within one minute, and more preferably within 30 seconds, which has conventionally been considered to be difficult to be prepared with a conventional compression molding machine, and having a practical hardness, by combining as additives (1) D-mannitol, (2) crospovidone and/or carmellose, and (3) sodium stearyl fumarate and/or a sucrose ester of fatty acids.

Concretely, the present relates to a tablet as listed hereinbelow:

[1] An oral disintegrating tablet containing (1) D-mannitol, (2) an active ingredient, (3) one or more disintegrating agents selected from the group consisting of crospovidone and carmellose, and (4) one or more lubricants selected from the group consisting of sodium stearyl fumarate and sucrose esters of fatty acids.

[2] The oral disintegrating tablet according to the above [1], wherein the disintegrating agent is crospovidone.

[3] The oral disintegrating tablet according to the above [1] or [2], wherein the lubricant is sodium stearyl fumarate.

[4] The oral disintegrating tablet according to any one of the above [1] to [3], wherein the disintegrating agent is present in an amount of from 1 to 10% by weight.

[5] The oral disintegrating tablet according to any one of the above [1] to [4], wherein the lubricant is present in an amount of from 0.01 to 5% by weight.

[6] The oral disintegrating tablet according to any one of the above [1] to [5], wherein the D-mannitol has an average particle size of greater than 10 μm and equal to or less than 500 μm.

[7] The oral disintegrating tablet according to any one of the above [1] to [6], wherein the D-mannitol has an average particle size of greater than 10 μm and equal to or less than 200 μm.

[8] The oral disintegrating tablet according to any one of the above [1] to [7], wherein the D-mannitol has an average particle size of greater than 30 μm and equal to or less than 150 μm.

[9] The oral disintegrating tablet according to any one of the above [1] to [8], wherein the D-mannitol has an average particle size of greater than 30 μm and a specific surface area of greater than 0.40 $m^2/g$.

[10] The oral disintegrating tablet according to any one of the above [1] to [9], wherein the D-mannitol is a β-type crystal.

[11] The oral disintegrating tablet according to any one of the above [1] to [10], further containing a binder.

[12] The oral disintegrating tablet according to the above [11], wherein the binder is one or more members selected from the group consisting of hydroxypropyl cellulose and pregelatinized starch (alpha-starch).

[13] The oral disintegrating tablet according to the above [12], wherein a 2% aqueous solution of the hydroxypropyl cellulose has a viscosity of from 2 to 10 mP·s at 20° C.

[14] The oral disintegrating tablet according to any one of the above [11] to [13], wherein the binder is present in an amount of from 0.01 to 2% by weight.

[15] The oral disintegrating tablet according to any one of the above [1] to [14], further containing a starch.

[16] The oral disintegrating tablet according to the above [15], wherein the starch is one or more members selected from the group consisting of corn starch, potato starch, rice starch, wheat starch, and partially pregelatinized starch.

[17] The oral disintegrating tablet according to any one of the above [1] to [16], wherein the active ingredient is amlodipine or a pharmacologically acceptable salt thereof.

[18] The oral disintegrating tablet according to any one of the above [1] to [17], wherein the active ingredient is amlodipine besylate.

[19] The oral disintegrating tablet according to any one of the above [1] to [18], wherein the active ingredient is a particle granulated or coated with a coating agent.

[20] The oral disintegrating tablet according to any one of the above [1] to [19], wherein the active ingredient is amlodipine, or a pharmacologically acceptable salt thereof, granulated or coated with a coating agent.

[21] The oral disintegrating tablet according to any one of the above [1] to [20], wherein the active ingredient is amlodipine besylate granulated or coated with a coating agent.

[22] An oral disintegrating tablet containing (1) D-mannitol having an average particle size of greater than 30 μm and a specific surface area of greater than 0.40 $m^2/g$, (2) 0.1 to 50% by weight of an active ingredient, (3) 1 to 10% by weight of crospovidone and/or carmellose, (4) 2% by weight or less of hydroxypropyl cellulose and/or pregelatinized starch, (5) 5 to 20% by weight of a starch, and (6) 0.1 to 5% by weight of sodium stearyl fumarate.

[23] The oral disintegrating tablet according to any one of the above [1] to [22], wherein the tablet disintegrates in the oral cavity within 30 seconds, and has an absolute hardness of 2.5 $N/mm^2$ or more.

[24] The oral disintegrating tablet according to any one of the above [1] to [23], wherein the tablet disintegrates in the oral cavity within 30 seconds, and has an absolute hardness of 3.0 $N/mm^2$ or more.

[25] The oral disintegrating tablet according to any one of the above [1] to [24], characterized in that the oral disintegrating tablet is produced using granules obtained by subjecting a mixture containing at least D-mannitol and a disintegrating agent to wet granulation.

[26] The oral disintegrating tablet according to any one of the above [1] to [25], wherein in a case where D-mannitol for direct compression is used as a D-mannitol, the proportion of the D-mannitol for direct compression is less than 50% by weight of all the D-mannitol in the formulation.

[27] The oral disintegrating tablet according to any one of the above [1] to [26], wherein in a case where D-mannitol for direct compression is used as a D-mannitol, the proportion of the D-mannitol for direct compression is less than 30% by weight of all the D-mannitol in the formulation.

Effects of the Invention

Since the oral disintegrating tablet of the present invention contains (1) D-mannitol, (2) crospovidone and/or carmellose, and (3) sodium stearyl fumarate and/or a sucrose ester of fatty acids, the tablet exhibits excellent effects of showing fast disintegrating ability and excellent ingestion feel in the oral cavity, and having an appropriate strength that does not breakdown in the process of distribution.

BRIEF DESCRIPTION OF THE DRAWINGS

FIG. 1 is a plot showing the test results of Formulation Examples 1 to 8. The axis of abscissas of the graph shows an absolute hardness, and the axis of ordinates shows a disintegration time with an oral disintegrating tablet tester. In FIG. 1, solid circles (●) are Formulation Example 1, solid triangles (▲) are Formulation Example 2, open circles (○) are Formulation Example 3, open triangles (Δ) are Formulation Example 4, open squares (□) are Formulation Example 5, open diamonds (◇) are Formulation Example 6, asterisks (*) are Formulation Example 7, and pluses (+) are Formulation Example 8.

BEST MODE FOR CARRYING OUT THE INVENTION

The present invention shall be explained more specifically hereinbelow.

In the present invention, the term "oral disintegrating tablet" means an ingestible tablet capable of being disintegrated with saliva alone in the oral cavity within 60 seconds, preferably within 45 seconds, and more preferably within 30 seconds, the tablet being disintegrated in the oral cavity without taking water. This disintegration time in the oral cavity can be measured with excellent reproducibility by using an oral disintegrating tablet tester (Toyama Sangyo Co., Ltd., Model ODT-101).

In the present invention, the term "absolute hardness" is a value obtained by dividing a tablet hardness by a broken area. In addition, a practical hardness refers to a hardness having a strength not only to an extent that a tablet does not breakdown upon taking out from the PTP (blister) package, but also to that applicable during the production and in the process of distribution, even in an automatic tablet packaging machine upon dispensing the dosage form. Specifically, the absolute hardness includes usually 1.5 $N/mm^2$ or more, preferably 2.0 $N/mm^2$ or more, more preferably 2.5 $N/mm^2$ or more, and even more preferably 3.0 $N/mm^2$ or more. Here, in the present invention, the tablet hardness can be measured using, for example, a tablet hardness tester TH-203MP (manufactured by Toyama Sangyo Co., Ltd.). Also, the broken area can be calculated from the tablet shape and the tablet thickness.

"D-Mannitol" has the tendencies that if its particle size is too small, the disintegrating ability is drastically lowered, while compression moldability is improved, and conversely that if its particle size is too large, compression moldability is worsened and the strength of a tablet is lowered, and also gives a gritty feel in the oral cavity, thereby worsening the ingestion feel. Therefore, it is preferable to use D-mannitol having an average particle size of greater than 10 μm and equal to or lower than 500 μm. Accordingly, the "D-mannitol" used in the present invention has an average particle size of preferably greater than 10 μm and equal to or lower than 500 μm, more preferably greater than 10 μm and equal to or lower than 200 μm, and even more preferably greater than 30 μm and equal to or lower than 150 μm. The average particle size as referred to herein is a median diameter on a volume basis, as measured by a dry method using a laser diffraction particle size distribution analyzer. For example, the average particle size can be measured using a laser diffraction particle size distribution analyzer SALD-3000 (manufactured by Shimadzu Corporation).

The "D-mannitol" used in present invention has a specific surface area of preferably greater than 0.20 $m^2/g$, more preferably greater than 0.30 $m^2/g$, even more preferably greater than 0.40 $m^2/g$ and less than 1.00 $m^2/g$, and still even more preferably greater than 0.40 $m^2/g$ and equal to or less than 0.80 $m^2/g$. Here, in the present invention, the specific surface area is a value measured by a multipoint BET method, and the specific surface area can be measured using, for example, a specific surface area measurement apparatus Tristar 3000 (manufactured by Micromeritics).

Therefore, a preferred example of the "D-mannitol" includes those having an average particle size of greater than 30 μm and a specific surface area of greater than 0.40 $m^2/g$.

Also, it is known that the D-mannitol exists in crystal polymorphisms of α, β and δ-types, and in the present invention the crystal form is not particularly limited. However, since the α- and δ-types relatively easily undergo crystal form transformation depending upon temperatures and humidity, it is preferable to use the β-type, which is the most stable form. The content in the formulation is not particularly limited, and the content is preferably 50% by weight or more, more preferably 60% by weight or more, and even more preferably 65% by weight or more, and the content is preferably 95% by weight or less, and more preferably 90% by weight or less. Here, as the D-mannitol, a D-mannitol for direct compression (also referred to as D-mannitol for direct tableting) can be used, and in that case, in order to maintain favorable disintegrating ability, it is preferable that the D-mannitol for direct compression is used in combination with a powder D-mannitol. The proportion of the D-mannitol for direct compression to all the D-mannitol in the formulation is preferably less than 50% by weight, more preferably less than 30% by weight, even more preferably less than 10% by weight, and still even more preferably substantially not containing any D-mannitol for direct compression. The phrase "for direct compression" as used herein refers to those worked to a form suitable for tableting according to mainly a direct tableting method, which is prepared by, for example, spray-drying.

"The disintegrating agent" includes crospovidone and carmellose, and preferably including crospovidone. The content in the formulation is not particularly limited, and the content includes preferably from 1 to 20% by weight, including more preferably from 1 to 10% by weight, including even more preferably from 2 to 10% by weight, and including still even more preferably 2 to 5% by weight. The content in the formulation of the total amount of the disintegrating agents in a case where one or more disintegrating agents are used is the same amount as the above.

In addition, to the tablet of the present invention, a disintegrating agent which is ordinarily used in the pharmaceutical field other than the above can be added, within the range that would not affect the effects of the present invention. The disintegrating agent includes, for example, croscarmellose sodium, carboxymethyl cellulose calcium, carboxymethyl starch sodium, and a low-substituted hydroxypropyl cellulose.

Further, since the tablet of the present invention further contains a starch, a more preferred disintegrating ability is obtained. The starch includes natural starches, such as corn starch, potato starch, rice starch, and wheat starch; and partially pregelatinized starches in which a part of the starches are pregelatinized. Here, the partially pregelatinized starch refers to those in which a part of the starch is pregelatinized, of which cold water-soluble content is from 0.5 to 20% by weight. The cold water-soluble content is measured by a method of adding to a weighed starch purified water at room temperature (20° C.) in an amount 10 times by weight of the weighed starch, stirring the mixture at 1,500 rpm for 2 minutes, centrifuging the resulting suspension at 1,500 rpm for 15 minutes, drying supernatant obtained from the centrifugation to give a residue, and obtaining the content in terms of % by weight obtained by dividing the residue by a total amount of the initially weighed starch. When the starch is used for the above purpose, the starch is added in a manner that the particle shape of the starch is substantially maintained. The content of the starch in the formulation is not particularly limited, and the content includes preferably 1 to 50% by weight, including more preferably 5 to 30% by weight, and including even more preferably 5 to 20% by weight.

The "lubricant" includes sodium stearyl fumarate and sucrose esters of fatty acids, from the viewpoint of controlling impediment upon tableting, especially controlling die friction, and including preferably sodium stearyl fumarate. The content in the formulation is not particularly limited, and the lubricant is usually used within the range of from 0.01 to 5% by weight, and including preferably within the range of from 0.01 to 4% by weight. In addition, in a case where an external lubricator is used, the content is preferably within the range of from 0.01 to 0.5% by weight, and in a case where the lubricant is mixed with a composition for compression, the content is preferably within the range of from 0.5 to 4% by weight. In addition, in a case where the lubricant is sodium stearyl fumarate, the content is preferably from 1.5 to 4% by weight. The content in the formulation of the entire amount of the lubricants in a case where one or more lubricants are used is the same amount as the above.

In addition, to the tablet of the present invention, a lubricant ordinarily used in the pharmaceutical field other than the above can be added, within the range that would not affect the effects of the present invention. The lubricant includes, for example, stearic acid, magnesium stearate, calcium stearate, talc, carnauba wax, L-leucine, and macrogols.

The tablet of the present invention may be added with a "binder" as occasion demands. Preferred binders include hydroxypropyl cellulose and pregelatinized starch.

The hydroxypropyl cellulose used as a binder for the tablet of the present invention preferably includes a hydroxypropyl cellulose of which 2% aqueous solution has a viscosity of from 2 to 10 mP·s at 20° C., for example, HPC-L (manufactured by Nippon Soda Co., Ltd., viscosity in 2% aqueous solution: 6.0 to 10.0 mPa·s). The content in the formulation is not particularly limited, and the content includes preferably 3% by weight or less. The content includes more preferably 2% by weight or less, including even more preferably from 0.01 to 2% by weight, and including still even more preferably from 0.1 to 1% by weight.

In a case where a pregelatinized starch is used as a binder, a natural starch such as corn starch or potato starch, or a partially pregelatinized starch is suspended in water, and the suspension is then heated to be pregelatinized, or a commercially available pregelatinized starch known under the trade name of Amycol C (manufactured by NIPPON STARCH CHEMICAL CO., LTD.) or a partially pregelatinized starch may be dissolved and used. The content of the pregelatinized starch in the formulation is not particularly limited, and the content includes preferably 3% by weight or less. The content includes more preferably 2% by weight or less, including even more preferably from 0.01 to 2% by weight, and including still even more preferably from 0.6 to 1.5% by weight.

In a case where one of more kinds of the binders are used, the content of the entire amount of the binders in the formulation is preferably 3% by weight or less, more preferably 2% by weight or less, and even more preferably from 0.01 to 2% by weight.

To the tablet of the present invention, a binder ordinarily used in the pharmaceutical field other the above can be added, within the range that would not affect the effects of the present invention. The binder includes, for example, polyvinyl alcohols, polyvinyl pyrrolidone (povidone), hydroxypropyl methyl cellulose (hypromellose), agar, and gelatin.

As the "active ingredient" of the tablet of the present invention, any drugs can be used so long as the drug can be formulated as a customary tablet. The drug used in the present invention may be in any forms, such as solid, crystalline, oily and solution forms. For example, and one or more ingredients selected from the group consisting of alimentary roborants, antipyretic analgesic antiphlogistics, psychotropic agents, anxiolytics, antidepressants, hypnotic sedatives, antispasmodics, central nervous system acting drugs, cerebral metabolism improving agents, cerebral circulation improving agents, antiepileptics, sympathomimetics, digestives, antacids, antiulcer agents, antitussive expectorants, antiemetics, respiratory stimulants, bronchodilators, antiallergic agents, dental stomatic agents, antihistamines, cardiacs, antiarrhythmic agents, diuretics, antihypertensive agents, angiotonics, coronary vasodilators, peripheral vasodilators, antihyperlipemic drugs, cholagogues, antibiotics, chemotherapeutics, antidiabetic agents, osteoporosis treating drugs, antirheumatics, skeletal muscle relaxants, antispasmodic drugs, hormone drugs, alkaloid narcotics, sulfa drugs, gout treating agents, anticoagulants, antineoplastic agents, and the like are used.

Concrete examples of the active ingredient are not particularly limited, so long as the active ingredient is intended for oral administration, and drugs of highly appreciative use include antipyretic antiphlogistics such as indomethacin, ibuprofen, ketoprofen, acetaminophen, aspirin, and isopropylantipyrine; antihistamines such as diphenylpyraline hydrochloride, chlorpheniramine maleate, cimetidine, and isothipendyl hydrochloride; cardiovascular drugs such as phenylephrine hydrochloride, procainamide hydrochloride, quinidine sulfate, and isosorbide nitrate; antihypertensives such as amlodipine besylate and arotinolol hydrochloride; tranquilizers such as sulpiride, diazepam, valproic acid, lithium carbonate, and tandospirone citrate; antibiotics such as cefalexin and ampicillin; peptides or proteins, such as insulin, vasopressin, interferon, interleukin-2, urokinase, and various growth factors, such as human growth hormones; and other drugs such as theophylline, caffeine, carbetapentane citrate, phenylpropanolamine hydrochloride, etidronate disodium, cetirizine hydrochloride, and droxidopa; and pharmaceutically acceptable salts thereof (including inorganic salts and organic salts).

In addition, these active ingredients may be "coated particles," in which a part or an entire part of the surface of the active ingredient is coated with a coating agent such as a water-insoluble polymer or a water-soluble polymer, for the purposes of masking bitterness, controlling bleeding out, stabilization, and the like.

The term "coated particles" in the present invention refer to particles obtained by depositing a solution or dispersion containing a coating agent or a melted liquid mixture thereof on a surface of an active ingredient or an active ingredient-containing composition, thereby covering all or a part of the surface of the particles.

The coating agent includes, for example, water-soluble polymers, water-insoluble polymers, gastro-soluble polymers, and enteric polymers. The water-soluble polymer is not particularly limited, and examples thereof include natural polymers and polysaccharides, such as gum arabic powder (powdered acacia), gelatin, pullulan, dextrin, carboxymethyl starch sodium, and sodium alginate, and derivatives thereof; cellulose derivatives such as carmellose, carmellose sodium, carmellose calcium, hydroxypropyl cellulose, hydroxypropylmethyl cellulose, hydroxyethyl cellulose, hydroxymethyl cellulose, methyl cellulose, and carboxymethyl cellulose; and water-soluble vinyl derivatives such as polyvinyl pyrrolidone and polyvinyl alcohol. The water-insoluble polymer is not particularly limited, and examples thereof include ethyl cellulose (especially, aqueous ethyl cellulose dispersion (for example, a product manufactured by FMC under the trade name of AQUACOAT)), vinyl acetate polymer (for example, a product manufactured by BASF under the trade name of Kollicoat SR30D), an aminoalkyl methacrylate copolymer (especially, aqueous dispersions thereof (ammonio methacrylate copolymer dispersion) (for example, products manufactured by EVONIC under the trade names of EUDRAGIT RL30D and EUDRAGIT RS30D)), an ethyl acrylate-methyl methacrylate copolymer dispersion (for example, a product manufactured by EVONIC under the trade name of EUDRAGIT NE30D). The gastro-soluble polymer is not particularly limited, and includes aminoacetal compounds, such as a polyvinyl acetal diethylamino acetate (for example, a product manufactured by Mitsubishi-Kagaku Foods Corporation under the trade name of AEA), an aminoalkyl methacrylate copolymer E (for example, a product manufactured by EVONIC under the trade name of EUDRAGIT E), and a mixture thereof. The enteric polymer is not particularly limited, and includes enteric cellulose esters, such as cellulose acetate propionate, hydroxypropyl methyl cellulose acetate succinate, hydroxypropylmethyl cellulose phthalate (phthalic ester of hypromellose), hydroxymethyl ethyl cellulose phthalate, carboxymethylethyl cellulose, and cellulose acetate phthalate; and enteric acrylic copolymers, such as a methacrylic acid copolymer LD (for example, a product manufactured by EVONIC under the trade name of EUDRAGIT L30D-55, a product manufactured by Sanyo Chemical Industries, Ltd. under the trade name of POLYQUID PA30, and a product manufactured by BASF under the trade name of Kollicoat MAE30DP), a methacrylic acid copolymer L (for example, a product manufactured by EVONIC under the trade name of EUDRAGIT L), a methacrylic copolymer S (for example, products manufactured by EVONIC under the trade names of EUDRAGIT S100 and EUDRAGIT FS30D).

An apparatus for coating includes general fluidized bed granulators (including tumbling fluidized bed granulators, Wurster fluidized bed granulators, and the like). In order to suppress the formation of coarse particles during the step, a fluidized bed granulator with an improved Wurster air suspension method, equipped with a forced circulation apparatus from the side surface (for example, SPC manufactured by Powrex Corporation, or the like) or a complex fluidized bed granulator equipped with a sizing and disintegrating mechanism (screen impeller means, blade stator means, cross-screw, lump-braker, or the like) (for example, particle coating and granulating apparatus SFP-01, manufactured by Powrex Corporation, or the like), and a rotary fluidized bed granulator (for example, OMNITEX manufactured by NARA MACHINERY CO., LTD., or the like) are preferred. As an apparatus for spray-drying, a general spray-dryer (a product manufactured by OKAWARA CORPORATION, OKAWARA KAKOKI, YAMATO, NIRO, or the like) can be used.

The content of the active ingredient in the formulation may differ depending upon the properties, and the content is usually 50% by weight or less, including preferably 30% by weight or less, and including more preferably 10% by weight or less, of the tablet.

In the formulation of the present invention, a nontoxic and inactive additive that is ordinarily used in the pharmaceutical field other than the above component can also be added, within the range that would not affect the effects of the present invention.

The additive to be used may be any pharmaceutically acceptable additives, including for example, excipients, fluidizing agents, sweeteners, corrigents, odorizing agents and flavoring agents, coloring agents, and stabilizing agents. The excipient includes, for example, saccharides, such as lactose, refined sugar, sucrose, fructose, fructo-oligosaccharide, glucose, maltose, reduced maltose, powder sugar, powdered candy, and reduced lactose; sugar alcohols such as erythritol, sorbitol, maltitol, and xylitol; kaolin, calcium hydrogenphosphate, calcium sulfate, calcium carbonate, and crystalline cellulose. The fluidizing agent includes, for example, a light anhydrous silicic acid, and magnesium aluminometasilicate. The sweetener and the corrigent include, for example, high-sweetness sweeteners, such as aspartame, saccharin, saccharin sodium, dipotassium glycyrrhizate, stevia, thaumatin, sucralose, and acesulfame K. Among them, preferred high-sweetness sweeteners include aspartame, thaumatin, and sucralose. The odorizing agent and the flavoring agent include, for example, peppermint, spearmint, menthol, lemon, orange, grapefruit, pineapple, fruits, and yoghurt. Depending upon the blending of the sweetener, the corrigent, the odorizing agent, and the flavoring agent mentioned above, a more preferred pleasant feel upon ingestion may be obtained in some cases. These additives can be appropriately added in proper amounts alone or in a combination of two or more kinds.

The method for producing a tablet of the present invention is not particularly limited, and the tablet can be, for example, produced according to the following method. A tablet can be obtained by mixing D-mannitol, a disintegrating agent, and a starch, granulating the mixture with water or an aqueous solution of a binder, drying the granulated product, mixing the dried product with an active ingredient and a lubricant, and subjecting the mixture to compression molding. The active ingredient may be mixed and granulated together with D-mannitol or the like. In a case where there is risk of inhibiting homogeneity of the content of the active ingredient, such as each component used has aggregating property, or contains a large crystal or granule, it is desired that each ingredient is regulated in size to a particle size that can ensure the homogeneity of the content by utilizing a means such as pulverization before or after mixing each ingredient. The molding method for a tablet is not particularly limited, and in a case where the tablet is commercially produced, a compression molding method employing a rotary tableting machine or a single-punch tableting machine is employed.

Here, in the tablet of the present invention, the compression molding can be carried out without using an external lubrication method, and as a matter of course, the molding can be also carried out with the external lubrication method. In this case, components excluding a lubricant is mixed, and thereafter tableting is carried out with molds (punches and dies), while spraying a lubricant thereto, or alternatively, a part of the lubricant is previously mixed, and thereafter tableting is carried out with molds, while spraying the remainder lubricant thereto.

The compression molding force is not particularly limited, so long as the molding force is to an extent that provides sufficient strength to the tablet, and the compression molding force of 1 kN (about 100 kgf) or more is preferred. The shape of the tablet obtained in the present invention is not particularly limited, and the tablet may take any shapes, such as disc-shaped tablet, disc-shaped R-tablet, disc-shaped tablet with beveled edge, and various heteromorphic tablets, and alternatively the tablet may be a scored tablet.

EXAMPLES

The present invention will be specifically described hereinbelow by the Examples, without intending to limit the scope of the present invention thereto. In the measurements of the physical property values, unless specified otherwise, the average particle size is a value which is obtained by a measurement according to a dry method using a laser diffraction particle size distribution analyzer SALD-3000 (manufactured by Shimadzu Corporation), and calculating a median diameter on a volume basis, which is defined as an average particle size, and the specific surface area is a value obtained by a measurement using a specific surface area measuring apparatus Tristar 3000 (manufactured by Micromeritics), and calculating according to a multipoint BET method, which is defined as a specific surface area.

Example 1

Eighty grams of hydroxypropyl cellulose (HPC-L, viscosity in a 2% aqueous solution: 6.0 to 10.0 mPa·s, manufactured by Nippon Soda Co., Ltd.) was dissolved in 2,320 g of purified water, to give 2,400 g of a binding liquid.

A fluidized bed granulator (Multiplex MP-01, manufactured by Powrex Corporation) was charged with 69.3 g of amlodipine besylate, 936.7 g of D-mannitol (β-type crystal, average particle size: 43 µm, specific surface area: 0.51 m$^2$/g), 100 g of corn starch (Corn Starch (XX16)W, manufactured by NIHON SHOKUHIN KAKO CO., LTD.), and 50 g of crospovidone (Polyplasdone XL-10, manufactured by ISP), and the contents were mixed. Thereafter, a 240 g portion of the above binding liquid was sprayed thereto and granulated, and dried, to give about 1,000 g of granules formed by granulation.

To 116.4 g of the granules formed by granulation were added 1.2 g of a light anhydrous silicic acid (Aerosil 200, manufactured by Nippon Aerosil Co., Ltd.) and 2.4 g of sodium stearyl fumarate (PRUV, manufactured by JRS PHARMA) while mixing, to give granules for tableting.

The resulting granules for tableting were subjected to tableting using a single-punch tableting machine (EK0, manufactured by KORSCH) at a compressive force of about 7 kN, to give a tablet having a diameter of 7 mm, a curvature radius of 10 mm, and a weight of 120 mg.

Example 2

Production of Amlodipine Besylate-Coated Particles

In 667.8 g of purified water was dissolved 37.35 g of polysorbate 80 (Polysorbate 80 (HX), manufactured by NOF Corporation), and subsequently 88.12 g of talc (TALCAN HAYASHI, manufactured by Hayashi-Kasei Co., Ltd.), 63.01 g of croscarmellose sodium (Ac-Di-Sol, manufactured by FMC) were mixed therewith, and the mixture was blended with a liquid mixture previously prepared by adding 83.99 g of a 1 N aqueous sodium hydroxide solution to 840 g of a methacrylic acid copolymer LD (POLYQUID PA-30S, manufactured by Sanyo Chemical Industries, Ltd.), to give a coating liquid.

Four-hundred grams of amlodipine besylate and 1.6 g of a light anhydrous silicic acid (Aerosil 200, manufactured by Nippon Aerosil Co., Ltd.) were sufficiently mixed in a polyethylene bag, and the mixture was supplied into a Wurster fluidized bed granulator equipped with a forced circulation apparatus (an improved Wurster fluidized bed granulator MP-01 SPC, manufactured by Powrex Corporation), and the above coating liquid was sprayed thereto. At a point where the amount sprayed was 1,595 g, the drying/film-forming step was carried out in the fluidized bed. The amlodipine besylate-coated particles had an average particle size of 88 μM.

Example 3

Anhydrous Caffeine-Coated Particles

In 188.5 g of purified water was dissolved 31.5 g of polysorbate 80 (Polysorbate 80 (HX), manufactured by NOF Corporation), and subsequently 700 g of a methacrylic acid copolymer LD (POLYQUID PA-30S, manufactured by Sanyo Chemical Industries, Ltd.) was added to mix, to give a coating liquid.

In a polyethylene bag were sufficiently mixed 346.6 g of anhydrous caffeine and 3.5 g of a light anhydrous silicic acid (Aerosil 200, manufactured by Nippon Aerosil Co., Ltd.), and the mixture was supplied into a Wurster fluidized bed granulator equipped with a forced circulation apparatus (an improved Wurster fluidized bed granulator MP-01 SPC, manufactured by Powrex Corporation), and the above coating liquid was sprayed thereto. At a point where the amount sprayed was 751.3 g, the drying/film-forming step was carried out in the fluidized bed. The anhydrous caffeine-coated particles had an average particle size of 127 μm.

Example 4

Eighty grams of hydroxypropyl cellulose (HPC-L, manufactured by Nippon Soda Co., Ltd.) was dissolved in 2,320 g of purified water, to give 2,400 g of a binding liquid.

A fluidized bed granulator (Multiplex MP-01, manufactured by Powrex Corporation) was charged with 864.25 g of D-mannitol (β-type crystal, average particle size: 43 μm, specific surface area: 0.51 m$^2$/g), 100 g of corn starch (Corn Starch (XX16)W, manufactured by NIHON SHOKUHIN KAKO CO., LTD.), and 50 g of crospovidone (Polyplasdone XL-10, manufactured by ISP), and the contents were mixed. Thereafter, a 240 g portion of the above binding liquid was sprayed to the mixture, and granulated, and dried, to give about 1,000 g of granules formed by granulation.

To 102.23 g of the granules formed by granulation were added 14.18 g of the amlodipine besylate-coated particles produced in Example 2, 1.2 g of a light anhydrous silicic acid (Aerosil 200, manufactured by Nippon Aerosil Co., Ltd.), and 2.4 g of sodium stearyl fumarate (PRUV, manufactured by JRS PHARMA), while mixing, to give granules for tableting.

The resulting granules for tableting were subjected to tableting using a single-punch tableting machine (EK0, manufactured by KORSCH) at a compressive force of about 7 kN, to give a tablet having a diameter of 7 mm, a curvature radius of 10 mm, and a weight of 120 mg.

Comparative Examples 1 and 2

A tablet having a diameter of 7 mm and a weight of 120 mg was obtained in the same manner as in Example 4, except that a D-mannitol (β-type crystal) shown in Table 1 was used in place of the D-mannitol having an average particle size of 43 μm and a specific surface area of 0.51 m$^2$/g.

TABLE 1

|  | Average Particle Size (μm) | Specific Surface Area (m$^2$/g) |
|---|---|---|
| Comp. Ex. 1 | 9 | 1.56 |
| Comp. Ex. 2 | 236 | 0.12 |

Example 5 and Comparative Examples 3 to 6

A tablet was obtained in the same manner as in Example 4, except that 2.4 g of sodium stearyl fumarate was changed to a lubricant shown in Table 2 and its amount supplied.

TABLE 2

|  | Lubricant | Amount Supplied (g) | Weight of Tablet (mg) |
|---|---|---|---|
| Ex. 5 | Sucrose esters of fatty acids (SURFHOPE SE PHARMA J-1803F, manufactured by Mitsubishi Kagaku) | 2.4 | 120 |
| Comp. Ex. 3 | Magnesium Stearate ((Light) Magnesium Stearate, vegetable, manufactured by Taihei Chemical Industrial Co., Ltd.) | 1.2 | 118.8 |
| Comp. Ex. 4 | Magnesium Stearate ((Light) Magnesium Stearate, vegetable, manufactured by Taihei Chemical Industrial Co., Ltd.) | 2.4 | 120 |
| Comp. Ex. 5 | Stearic Acid (Stearic Acid A, manufactured by NIPPON FINE SEIKA CO., LTD.) | 1.2 | 118.8 |
| Comp. Ex. 6 | Stearic Acid (Stearic Acid A, manufactured by NIPPON FINE SEIKA CO., LTD.) | 2.4 | 120 |

Example 6

A tablet having a diameter of 7 mm and a weight of 120 mg was obtained in the same manner as in Example 4, except that 50 g of crospovidone was changed to 50 g of carmellose (NS-300, manufactured by GOTOKU CHEMICAL COMPANY LTD.).

Example 7

A tablet having a diameter of 7 mm and a weight of 120 mg was obtained in the same manner as in Example 4, except that the binding liquid used was changed to 240 g of a liquid composed of 8 g of pregelatinized starch (Amycol C, manufactured by NIPPON STARCH CHEMICAL CO., LTD.) and 232 g of purified water.

Example 8

A tablet having a diameter of 7 mm and a weight of 121.6 mg was obtained in the same manner as in Example 4, except that 14.18 g of the amlodipine besylate-coated particles were changed to 15.79 g of the anhydrous caffeine-coated particles described in Example 3.

Test Example 1

The presence or absence of tableting impediment upon tableting was evaluated for Examples 1 and 4 to 8 and Comparative Examples 1 to 6 in three ranks (○: excellent, Δ: slight impediment, and x: notable impediment). The results are shown in Table 3. In a case where the impediment is generated, the kind of impediment is described within the parenthesis.

TABLE 3

| | Evaluation Results |
|---|---|
| Ex. 1 | ○ |
| Ex. 4 | ○ |
| Comp. Ex. 1 | Δ (Punch Clouding) |
| Comp. Ex. 2 | ○ |
| Ex. 5 | Δ (Punch Clouding) |
| Comp. Ex. 3 | X (Die Friction) |
| Comp. Ex. 4 | Δ (Die Friction) |
| Comp. Ex. 5 | X (Die Friction) |
| Comp. Ex. 6 | X (Die Friction) |
| Ex. 6 | ○ |
| Ex. 7 | ○ |
| Ex. 8 | ○ |

Test Example 2

The disintegration time was measured for the tablets produced according to Examples 1 and 4 to 8 and Comparative Examples 1, 2, and 4, with an oral disintegrating tablet tester (Toyama Sangyo Co., Ltd., Model ODT-101) under the conditions that a test solution was water (37°±1° C.), a mass of weight was 10 g and a rotational speed was 25 r/min. In addition, hardness was measured with a tablet hardness tester (Toyama Sangyo Co., Ltd., TH-203 MP). The resulting hardness is expressed as an absolute hardness of a value obtained by dividing hardness by an area of a broken cross section of a tablet. Further, the ingestion feel upon lingering a tablet in the mouth to allow complete disintegration was judged in three ranks (○: excellent, Δ: fair (normal), and x: poor), and the judgments for Δ and x are shown with the detailed ingestion feel in the parenthesis. The results are shown in Table 4.

TABLE 4

| | Disintegration Time (sec) | Hardness (N) | Absolute Hardness (N/mm$^2$) | Ingestion Feel |
|---|---|---|---|---|
| Ex. 1 | 18 | 45 | 2.5 | ○ |
| Ex. 4 | 20 | 51 | 2.7 | ○ |
| Comp. Ex. 1 | 34 | 64 | 3.3 | Δ (Poor dissolubility in mouth) |
| Comp. Ex. 2 | 20 | 39 | 2.1 | X (Gritty feel) |
| Ex. 5 | 17 | 50 | 2.7 | ○ |
| Comp. Ex. 4 | 38 | 48 | 2.6 | Δ (Poor dissolubility in mouth) |
| Ex. 6 | 24 | 47 | 2.5 | ○ |
| Ex. 7 | 14 | 49 | 2.6 | ○ |
| Ex. 8 | 25 | 53 | 2.8 | ○ |

As shown in Table 4, the tablets of Examples 1 and 4 to 7 all show excellent hardness (2.5 N/mm$^2$ or more) and a disintegration time (30 seconds or less), and had excellent ingestion feel. On the other hand, the tablet of Comparative Example 1 had a slow disintegration time, though showing excellent hardness. Also, the tablet of Comparative Example 2 had low hardness and gave gritty feel upon ingestion, though showing excellent disintegration time. The tablet of Comparative Example 4 had a slow disintegration time, though showing excellent hardness.

Example 2-1

Formulation Example 1

Eighty grams of hydroxypropyl cellulose (HPC-L, manufactured by Nippon Soda Co., Ltd.) was dissolved in 2,320 g of purified water, to give 2,400 g of a binding liquid.

A fluidized bed granulator (Multiplex MP-01, manufactured by Powrex Corporation) was charged with 69.3 g of amlodipine besylate, 936.7 g of D-mannitol (β-type crystal, average particle size: 43 μm, specific surface area: 0.51 m$^2$/g), 100 g of corn starch (Corn Starch (XX16)W, manufactured by NIHON SHOKUHIN KAKO CO., LTD.), and 50 g of crospovidone (Polyplasdone XL-10, manufactured by ISP), and the contents were mixed. Thereafter, a 240 g portion of the above binding liquid was sprayed thereto and granulated, and dried, to give granules formed by granulation.

To 116.4 g of the granules formed by granulation were added 1.2 g of a light anhydrous silicic acid (Aerosil 200, manufactured by Nippon Aerosil Co., Ltd.) and 2.4 g of sodium stearyl fumarate (PRUV, manufactured by JRS PHARMA) while mixing, to give granules for tableting.

The resulting granules for tableting were subjected to tableting using a single-punch tableting machine (EK0, manufactured by KORSCH) at compressive forces of 7 kN, 9 kN, and 11 kN, respectively, to give a tablet having a diameter of 7 mm, a curvature radius of 10 mm, and a weight of 120 mg. Here, the tablet obtained by tableting at a compressive force of 7 kN is a tablet equivalent to that of Example 1.

Example 2-2 and Comparative Examples 2-1 to -6

Formulation Examples 2 to 8

A tablet having a diameter of 7 mm, a curvature radius of 10 mm, and a weight of 120 mg was obtained in the same manner as in Formulation Example 1, except that 50 g of the crospovidone was changed to a disintegrating agent shown in Table 5.

TABLE 5

| | | Disintegrating Agent | Amount Supplied (g) |
|---|---|---|---|
| Ex. 2-1 | Formulation Ex. 1 | Crospovidone (Polyplasdone XL-10) | 50 |
| Ex. 2-2 | Formulation Ex. 2 | Carmellose (NS-300) | 50 |
| Comp. Ex. 2-1 | Formulation Ex. 3 | Low-substituted Hydroxypropyl Cellulose (L-HPC (LH-21)) | 50 |
| Comp. Ex. 2-2 | Formulation Ex. 4 | Croscarmellose Calcium (ECG-505) | 50 |
| Comp. Ex. 2-3 | Formulation Ex. 5 | Carmellose Sodium (Ac-Di-Sol) | 50 |
| Comp. Ex. 2-4 | Formulation Ex. 6 | Partially Pregelatinized Starch (PCS) | 50 |
| Comp. Ex. 2-5 | Formulation Ex. 7 | Carboxymethyl Starch Sodium (EXPLOTAB) | 50 |
| Comp. Ex. 2-6 | Formulation Ex. 8 | Hydroxypropyl Starch (HPS-101) | 50 |

Example 2-3

Formulation Example 9

A tablet having a diameter of 7 mm, a curvature radius of 10 mm, and a weight of 120 mg was obtained in the same manner as in Formulation Example 1, except that 100 g of corn starch (Corn Starch (XX16)W, manufactured by NIHON SHOKUHIN KAKO CO., LTD.) was replaced with the same amount of D-mannitol (β-type crystal, average particle size: 43 μm, specific surface area: 0.51 m$^2$/g), and that tableting was carried out at compressive forces of 6 kN and 9 kN.

Comparative Example 2-7

Formulation Example 10

A tablet having a diameter of 7 mm, a curvature radius of 10 mm, and a weight of 120 mg was obtained in the same manner as in Formulation Example 1, except that 936.7 g of the D-mannitol was replaced with the same amount of lactose (Pharmatose 200M), and that tableting was carried out at compressive forces of 7 kN and 9 kN.

Test Example 3

Hardness was measured for the formulations of Formulation Examples 1 to 10 and an absolute hardness was calculated, in the same manner as in Test Example 2. In addition, the disintegration time was measured in the same manner as in Test Example 2. The results are shown in Table 6, Table 7, and FIG. 1.

TABLE 6

| | | 7 kN | | 9 kN | | 11 kN | |
|---|---|---|---|---|---|---|---|
| | | Disintegration Time (sec) | Absolute Hardness (N/mm$^2$) | Disintegration Time (sec) | Absolute Hardness (N/mm$^2$) | Disintegration Time (sec) | Absolute Hardness (N/mm$^2$) |
| Ex. 2-1 | Formulation Ex. 1 | 18 | 2.5 | 17 | 3.7 | 17 | 4.4 |
| Ex. 2-2 | Formulation Ex. 2 | 24 | 2.0 | 25 | 2.8 | 26 | 4.1 |
| Comp. Ex. 2-1 | Formulation Ex. 3 | 22 | 2.1 | 31 | 2.8 | 42 | 3.0 |
| Comp. Ex. 2-2 | Formulation Ex. 4 | 30 | 2.2 | 36 | 3.4 | 44 | 4.2 |
| Comp. Ex. 2-3 | Formulation Ex. 5 | 26 | 2.1 | 34 | 3.2 | 45 | 4.3 |
| Comp. Ex. 2-4 | Formulation Ex. 6 | 27 | 1.5 | 33 | 2.5 | 45 | 4.1 |
| Comp. Ex. 2-5 | Formulation Ex. 7 | 18 | 1.8 | 34 | 2.6 | 41 | 4.0 |
| Comp. Ex. 2-6 | Formulation Ex. 8 | 22 | 1.5 | 26 | 2.3 | 42 | 3.8 |

TABLE 7

| | | 6 kN | | 7 kN | | 9 kN | |
|---|---|---|---|---|---|---|---|
| | | Disintegration Time (sec) | Absolute Hardness (N/mm$^2$) | Disintegration Time (sec) | Absolute Hardness (N/mm$^2$) | Disintegration Time (sec) | Absolute Hardness (N/mm$^2$) |
| Ex. 2-3 | Formulation Ex. 9 | 28 | 2.5 | — | — | 34 | 3.3 |
| Comp. Ex. 2-7 | Formulation Ex. 10 | — | — | 43 | 1.6 | 38 | 2.5 |

From the results of Tables 6 and 7, each of the formulations of Formulation Example 1 molded at a compressive force of 7, 9, or 11 kN, each of the formulations of Formulation Example 2 molded at a compressive force of 9 or 11 kN, and the formulation of Formulation Example 9 molded at a compressive force of 6 kN had a strength that the absolute hardness was 2.5 N/mm$^2$ or more, and at the same time had excellent disintegrating ability that the disintegration time was within 30 seconds. Especially, each of the formulations of Formulation Example 1 molded at a compressive force of 9 or 11 kN, the formulation of Formulation Example 2 molded at a compressive force of 11 kN had a surprising strength that the absolute strength was 3.0 N/mm$^2$ or more, while having excellent disintegrating ability that the disintegration time was within 30 seconds.

On the other hand, each of the formulations of Formulation Examples 3 to 8 in which a disintegrating agent other than crospovidone and carmellose was used, and the formulation of Formulation Example 10 in which lactose was used in place of the D-mannitol were not formulations that showed excellent properties that the absolute hardness was 2.5 N/mm$^2$ or more, and a disintegration time was within 30 seconds.

FIG. 1 is a plot showing the test results of Formulation Examples 1 to 8, in which the axis of abscissas of the graph is an absolute hardness, and the axis of ordinates is a disintegration time according to an oral disintegrating tablet tester. In the formulations of Formulation Examples 3 to 8, the extension of the disintegration time was observed with the increase in hardness; on the other hand, in Formulation Example 1 in which crospovidone was used for a disintegrating agent, and Formulation Example 2 in which carmellose was used therefor, the delay in the disintegration time with the increase in the hardness of the tablet was not observed. Due to the unexpected phenomena, it was considered that the formulation in which crospovidone or carmellose was used for a disintegrating agent can have both a high tablet strength and excellent disintegrating ability.

Example 3-1

Formulation Example 11

Eighty grams of hydroxypropyl cellulose (HPC-L, manufactured by Nippon Soda Co., Ltd.) was dissolved in 2,320 g of purified water, to give 2,400 g of a binding liquid.

A fluidized bed granulator (Multiplex MP-01, manufactured by Powrex Corporation) was charged with 864.25 g of D-mannitol (β-type crystal, average particle size: 43 μm, specific surface area: 0.51 m$^2$/g), 100 g of corn starch (Corn Starch (XX16)W, manufactured by NIHON SHOKUHIN KAKO CO., LTD.), and 50 g of crospovidone (Polyplasdone XL-10, manufactured by ISP), and the contents were mixed. Thereafter, a 240 g portion of the above binding liquid was sprayed thereto and granulated, and dried, to give about 1,000 g of granules formed by granulation.

To 102.23 g of the granules formed by granulation were added 14.18 g of the amlodipine besylate-coated particles produced in Example 2, 1.2 g of a light anhydrous silicic acid (Aerosil 200, manufactured by Nippon Aerosil Co., Ltd.), and 2.4 g of sodium stearyl fumarate (PRUV, manufactured by JRS PHARMA) while mixing, to give granules for tableting.

The resulting granules for tableting were subjected to tableting using a single-punch tableting machine (EK0, manufactured by KORSCH) at compressive forces of 7 kN and 9 kN, respectively, to give a tablet having a diameter of 7 mm, a curvature radius of 10 mm, and a weight of 120 mg.

Example 3-2 and Comparative Examples 3-1 to -6

Formulation Examples 12 to 18

A tablet having a diameter of 7 mm, a curvature radius of 10 mm, and a weight of 120 mg was obtained in the same manner as in Formulation Example 11, except that 50 g of crospovidone was changed to a disintegrating agent shown in Table 8, and that tableting was carried out at a compressive force shown in Table 9.

TABLE 8

| | | Disintegrating Agent | Amount Supplied (g) |
|---|---|---|---|
| Ex. 3-1 | Formulation Ex. 11 | Crospovidone (Polyplasdone XL-10) | 50 |
| Ex. 3-2 | Formulation Ex. 12 | Carmellose (NS-300) | 50 |
| Comp. Ex. 3-1 | Formulation Ex. 13 | Low-substituted Hydroxypropyl Cellulose (L-HPC (LH-21)) | 50 |
| Comp. Ex. 3-2 | Formulation Ex. 14 | Carmellose Calcium (ECG-505) | 50 |
| Comp. Ex. 3-3 | Formulation Ex. 15 | Croscarmellose Sodium (Ac-Di-Sol) | 50 |
| Comp. Ex. 3-4 | Formulation Ex. 16 | Partially Pregelatinized Starch (PCS) | 50 |
| Comp. Ex. 3-5 | Formulation Ex. 17 | Carboxymethyl Starch Sodium (EXPLOTAB) | 50 |
| Comp. Ex. 3-6 | Formulation Ex. 18 | Hydroxypropyl Starch (HPS-101) | 50 |

Example 3-3

Formulation Example 19

A tablet having a diameter of 7 mm and a weight of 121.6 mg was obtained in the same manner as in Formulation Example 11, except that 14.18 g of the amlodipine besylate-coated particles were changed to 15.79 g of the anhydrous caffeine-coated particles described in Example 3.

Example 3-4

Formulation Example 20

Forty-eight grams of triethyl citrate (CITROFLEX 2) was sufficiently dispersed in 700 g of purified water, and 1,400 g of an aqueous dispersion of ethyl cellulose (AQUACOAT, manufactured by FMC) was mixed with the dispersed solution, and 63 g of talc (TALCAN HAYASHI, manufactured by Hayashi-Kasei Co., Ltd.) was further added thereto, to give a coating liquid.

Four-hundred grams of amlodipine besylate and 1.6 g of a light anhydrous silicic acid (Aerosil 200, manufactured by Nippon Aerosil Co., Ltd.) were sufficiently mixed in a polyethylene bag, and the mixture was supplied into a Wurster fluidized bed granulator equipped with a forced circulation apparatus (an improved Wurster fluidized bed granulator MP-01 SPC, manufactured by Powrex Corporation), and the above coating liquid was sprayed thereto. At a point where the amount sprayed was 907 g, the drying/film-forming step was carried out in the fluidized bed, to give amlodipine besylate- and ethyl cellulose-coated particles.

A tablet having a diameter of 7 mm, a curvature radius of 10 mm, and a weight of 117.5 mg was obtained in the same manner as in Formulation Example 11, except that 14.18 g of the amlodipine besylate-coated particles were changed to 11.69 g of the amlodipine besylate- and ethyl cellulose-coated particles, and that tableting was carried out at a compressive force shown in Table 9.

Test Example 4

Hardness was measured for the formulations of Formulation Examples 11 to 20 and an absolute hardness was calculated, in the same manner as in Test Example 2. In addition, the disintegration time was measured in the same manner as in Test Example 2. The results are shown in Table 9.

TABLE 9

|  |  | 7 kN | | 9 kN | | 11 kN | |
| --- | --- | --- | --- | --- | --- | --- | --- |
|  |  | Disintegration Time (sec) | Absolute Hardness (N/mm$^2$) | Disintegration Time (sec) | Absolute Hardness (N/mm$^2$) | Disintegration Time (sec) | Absolute Hardness (N/mm$^2$) |
| Ex. 3-1 | Formulation Ex. 11 | 20 | 2.7 | 19 | 3.6 | — | — |
| Ex. 3-2 | Formulation Ex. 12 | 24 | 2.5 | 25 | 3.7 | — | — |
| Comp. Ex. 3-1 | Formulation Ex. 13 | 43 | 2.7 | — | — | — | — |
| Comp. Ex. 3-2 | Formulation Ex. 14 | 51 | 2.7 | — | — | — | — |
| Comp. Ex. 3-3 | Formulation Ex. 15 | 47 | 2.7 | — | — | — | — |
| Comp. Ex. 3-4 | Formulation Ex. 16 | 45 | 2.4 | — | — | — | — |
| Comp. Ex. 3-5 | Formulation Ex. 17 | 38 | 2.7 | — | — | — | — |
| Comp. Ex. 3-6 | Formulation Ex. 18 | 41 | 2.7 | — | — | — | — |
| Ex. 3-3 | Formulation Ex. 19 | 25 | 2.8 | 22 | 3.9 | — | — |
| Ex. 3-4 | Formulation Ex. 20 | 28 | 2.6 | — | — | 28 | 3.3 |

From the results of Table 9, each of the formulations of Formulation Examples 11, 12, 19, and 20 molded at a compressive force of 7 kN had a strength that the absolute hardness was 2.5 N/mm$^2$ or more, and at the same time had excellent disintegrating ability that the disintegration time was within 30 seconds. In addition, each of the formulations of Formulation Examples 11, 12, and 19 molded at a compressive force of 9 kN, and the formulation of Formulation Example 20 molded at a compressive force of 11 kN had a surprising strength that the absolute strength was 3.0 N/mm$^2$ or more, while having excellent disintegrating ability that the disintegration time was within 30 seconds.

On the other hand, each of the formulations of Formulation Examples 13 to 18 in which a disintegrating agent other than crospovidone and carmellose was used were not formulations that showed excellent properties that the absolute hardness was 2.5 N/mm$^2$ or more, and a disintegration time was within 30 seconds.

Comparative Example 4-1

Formulation Example 21

In 623.7 g of purified water was dispersed 6.3 g of corn starch (Corn Starch (XX16)W, manufactured by NIHON SHOKUHIN KAKO CO., LTD.), and the dispersion was heated to form a glue, to give 630 g of a binding liquid.

A fluidized bed granulator (Multiplex MP-01, manufactured by Powrex Corporation) was charged with 869.4 g of D-mannitol (β-type crystal, average particle size: 46 μm, specific surface area: 0.46 m$^2$/g), 90 g of corn starch (Corn Starch (XX16)W, manufactured by NIHON SHOKUHIN KAKO CO., LTD.), and 32.4 g of a low-substituted hydroxypropyl cellulose (L-HPC LH-22, manufactured by Shin-Etsu Chemical Co., Ltd.), and the contents were mixed. Thereafter, 630 g of the above binding liquid was sprayed thereto and granulated, and dried, to give granules formed by granulation.

To 99.81 g of the granules formed by granulation were added 14.18 g of the amlodipine besylate-coated particles produced in Example 2, 1.2 g of a light anhydrous silicic acid (Aerosil 200, manufactured by Nippon Aerosil Co., Ltd.), and 2.4 g of sodium stearyl fumarate (PRUV, manufactured by JRS PHARMA) while mixing, to give granules for tableting.

The resulting granules for tableting were subjected to tableting using a single-punch tableting machine (EK0, manufactured by KORSCH) at compressive forces of 6 kN and 7 kN, respectively, to give a tablet having a diameter of 7 mm, a curvature radius of 10 mm, and a weight of 120 mg.

Test Example 5

Hardness was measured for the formulation of Formulation Example 21 and an absolute hardness was calculated, in the same manner as in Test Example 2. In addition, the disintegration time was measured in the same manner as in Test Example 2. The results are shown in Table 10.

TABLE 10

|  |  | 6 kN | | 7 kN | |
| --- | --- | --- | --- | --- | --- |
|  |  | Disintegration Time (sec) | Absolute Hardness (N/mm$^2$) | Disintegration Time (sec) | Absolute Hardness (N/mm$^2$) |
| Comp. Ex. 4-1 | Formulation Ex. 21 | 36 | 2.7 | 46 | 3.1 |

From the results of Table 10, the formulation of Formulation Example 21, even when molded at both the compressive forces of 6 and 7 kN, showed an absolute hardness of 2.5 N/mm$^2$ or more, but the disinterating time exceeded 30 seconds.

Example 5-1

Formulation Example 22

Eighty grams of hydroxypropyl cellulose (HPC-L, manufactured by Nippon Soda Co., Ltd.) was dissolved in 2,320 g of purified water, to give 2,400 g of a binding liquid.

A fluidized bed granulator (Multiplex MP-01, manufactured by Powrex Corporation) was charged with 906 g of D-mannitol (β-type crystal, average particle size: 46 μm, specific surface area: 0.46 m$^2$/g), 100 g of corn starch (Corn Starch (XX16)W, manufactured by NIHON SHOKUHIN KAKO CO., LTD.), and 50 g of crospovidone (Polyplasdone XL-10, manufactured by ISP), and the contents were mixed. Thereafter, a 240 g portion of the above binding liquid was sprayed thereto and granulated, and dried, to give granules formed by granulation.

To 106.4 g of the granules formed by granulation were added 10 g of amlodipine besylate (average particle size: 20 μm), 1.2 g of a light anhydrous silicic acid (Aerosil 200, manufactured by Nippon Aerosil Co., Ltd.) and 3.6 g of sodium stearyl fumarate (PRUV, manufactured by JRS PHARMA) while mixing, to give granules for tableting.

The resulting granules for tableting were subjected to tableting using a single-punch tableting machine (EK0, manufactured by KORSCH) at a compressive force of 9 kN, to give a tablet having a diameter of 7 mm, a curvature radius of 10 mm, and a weight of 121.2 mg.

Examples 5-2 to -5

Formulation Examples 23 to 26

A tablet having a diameter of 7 mm, a curvature radius of 10 mm, and a weight of 121.2 mg was obtained in the same manner as in Formulation Example 22, except that 10 g of the amlodipine besylate was changed to an active ingredient shown in Table 11, and that tableting was carried out with a compressive force shown in Table 11.

TABLE 11

| | | Active Ingredient | Amount Supplied (g) | Tableting Compressive Force (kN) |
|---|---|---|---|---|
| Ex. 5-1 | Formulation Ex. 22 | Amlodipine Besylate | 50 | 9 |
| Ex. 5-2 | Formulation Ex. 23 | Metformlin Hydrochloride | 50 | 11 |
| Ex. 5-3 | Formulation Ex. 24 | Acetaminophen | 50 | 11 |
| Ex. 5-4 | Formulation Ex. 25 | Sodium Ascorbate | 50 | 11 |
| Ex. 5-5 | Formulation Ex. 26 | Ibuprofen | 50 | 11 |

Example 6-1

Formulation Example 27

Eighty grams of hydroxypropyl cellulose (HPC-L, manufactured by Nippon Soda Co., Ltd.) was dissolved in 2,320 g of purified water, to give 2,400 g of a binding liquid.

A universal mixing agitator (5DMr, manufactured by San-ei Seisakusho) was charged with 34.65 g of amlodipine besylate, 468.35 g of D-mannitol (β-type crystal, average particle size: 46 μm, specific surface area: 0.46 m$^2$/g), 5 g of corn starch (Corn Starch (XX16)W, manufactured by NIHON SHOKUHIN KAKO CO., LTD.), and 25 g of crospovidone (Polyplasdone XL-10, manufactured by ISP), and the contents were mixed. Thereafter, a 120 g portion of the above binding liquid was sprayed thereto, 20 g of purified water was added thereto, and the mixture was kneaded together. The kneaded mixture was dried on a shelf overnight with an aerating dryer at 60° C., and the dried mixture was subjected to sizing, to give granules formed by granulation.

To 116.4 g of the granules formed by granulation were added 1.2 g of a light anhydrous silicic acid (Aerosil 200, manufactured by Nippon Aerosil Co., Ltd.) and 2.4 g of sodium stearyl fumarate (PRUV, manufactured by JRS PHARMA) while mixing, to give granules for tableting.

The resulting granules for tableting were subjected to tableting using a single-punch tableting machine (EK0, manufactured by KORSCH) at a compressive force of 9 kN, to give a tablet having a diameter of 7 mm, a curvature radius of 10 mm, and a weight of 120 mg.

Example 6-2

Formulation Example 28

A universal mixing agitator (5DMr, manufactured by San-ei Seisakusho) was charged with 432.1 g of D-mannitol (β-type crystal, average particle size: 46 μm, specific surface area: 0.46 m$^2$/g), 50 g of corn starch (Corn Starch (XX16)W, manufactured by NIHON SHOKUHIN KAKO CO., LTD.), and 25 g of crospovidone (Polyplasdone XL-10, manufactured by ISP), and the contents were mixed. Thereafter, a 120 g portion of the binding liquid described in Formulation Example 27 was sprayed thereto, 20 g of purified water was further added thereto, and the mixture was kneaded together. The kneaded mixture was dried on a shelf overnight with an aerating dryer at 60° C., and the dried mixture was subjected to sizing, to give granules formed by granulation.

To 102.2 g of the granules formed by granulation were added 14.18 g of the amlodipine besylate-coated particles produced in Example 2, 1.2 g of a light anhydrous silicic acid (Aerosil 200, manufactured by Nippon Aerosil Co., Ltd.) and 2.4 g of sodium stearyl fumarate (PRUV, manufactured by JRS PHARMA) while mixing, to give granules for tableting.

The resulting granules for tableting were subjected to tableting using a single-punch tableting machine (EK0, manufactured by KORSCH) at a compressive force of 9 kN, to give a tablet having a diameter of 7 mm, a curvature radius of 10 mm, and a weight of 120 mg.

Example 6-3

Formulation Example 29

A tablet having a diameter of 7 mm, a curvature radius of 10 mm, and a weight of 120 mg was obtained in the same manner as in Formulation Example 28, except that 25 g of crospovidone was changed to 25 g of carmellose.

Example 6-4

Formulation Example 30

The granules for tableting in Example 5 were subjected to tableting using a single-punch tableting machine (EK0, manufactured by KORSCH) at a compressive force of 9 kN, to give a tablet having a diameter of 7 mm, a curvature radius of 10 mm, and a weight of 120 mg.

Example 6-5

Formulation Example 31

The granules for tableting in Example 7 were subjected to tableting using a single-punch tableting machine (EK0, manufactured by KORSCH) at a compressive force of 9 kN, to give a tablet having a diameter of 7 mm, a curvature radius of 10 mm, and a weight of 120 mg.

Test Example 6

Hardness was measured for the formulations of Formulation Examples 22 to 31 and an absolute hardness was calculated, in the same manner as in Test Example 2. In addition, the disintegration time was measured in the same manner as in Test Example 2. The results are shown in Table 12.

TABLE 12

|  |  | Disintegration Time (sec) | Absolute Hardness (N/mm$^2$) |
|---|---|---|---|
| Ex. 5-1 | Formulation Ex. 22 | 19 | 3.5 |
| Ex. 5-2 | Formulation Ex. 23 | 30 | 3.2 |
| Ex. 5-3 | Formulation Ex. 24 | 14 | 3.5 |
| Ex. 5-4 | Formulation Ex. 25 | 30 | 3.5 |
| Ex. 5-5 | Formulation Ex. 26 | 19 | 3.0 |
| Ex. 6-1 | Formulation Ex. 27 | 20 | 4.1 |
| Ex. 6-2 | Formulation Ex. 28 | 24 | 3.7 |
| Ex. 6-3 | Formulation Ex. 29 | 26 | 3.4 |
| Ex. 6-4 | Formulation Ex. 30 | 20 | 4.0 |
| Ex. 6-5 | Formulation Ex. 31 | 16 | 3.7 |

From the results of Table 12, all of the formulations of Formulation Examples 22 to 31 were formulations showing an absolute hardness of 3.0 N/mm$^2$ or more and a disintegration time of within 30 seconds.

INDUSTRIAL APPLICABILITY

The oral disintegrating tablet of the present invention has some excellent properties of (1) allowing easy production in a common facility without necessitating a specialized pharmaceutical technique, (2) having an appropriate strength that does not breakdown in the process of distribution, (3) having a fast disintegrating ability in the oral cavity, and (4) also having excellent ingestion feel such as greatly reduced bitterness or gritty feel; therefore, the tablet can be suitably used as a dosage form that is suitable for aged individuals, children, and seriously ill patients.

The invention claimed is:

1. An oral disintegrating tablet, comprising:
   (1) D-mannitol;
   (2) an active ingredient;
   (3) at least one disintegrating agent selected from the group consisting of crospovidone and carmellose;
   (4) at least one lubricant selected from the group consisting of sodium stearyl fumarate and sucrose esters of fatty acids;
   (5) at least one binder selected from the group consisting of hydroxypropyl cellulose, pregelatinized starch, polyvinyl alcohol, povidone, hydroxypropylmethylcellulose, agar, and gelatin, in an amount of less than 3% by weight; and
   (6) a starch,
   wherein the tablet disintegrates in an oral cavity within 30 seconds and has an absolute hardness of 2.5 N/mm$^2$ or more.

2. The oral disintegrating tablet of claim 1, wherein the at least one disintegrating agent is crospovidone.

3. The oral disintegrating tablet of claim 1 or 2, wherein the at least one lubricant is sodium stearyl fumarate.

4. The oral disintegrating tablet of claim 1, comprising the at least one disintegrating agent in an amount of from 1 to 10% by weight.

5. The oral disintegrating tablet of claim 1, comprising the at least one lubricant in an amount of from 0.01 to 5% by weight.

6. The oral disintegrating tablet of claim 1, wherein the D-mannitol is particulate and
   an average particle size of the particulate D-mannitol is greater than 10 µm and equal to or less than 500 µm.

7. The oral disintegrating tablet of claim 6, wherein an average particle size of the particulate D-mannitol is greater than 10 µm and equal to or less than 200 µm.

8. The oral disintegrating tablet of claim 7, wherein an average particle size of the particulate D-mannitol is greater than 30 µm and equal to or less than 150 µm.

9. The oral disintegrating tablet of claim 1, wherein an average particle size of the particulate D-mannitol is greater than 30 µm and a specific surface area of the D-mannitol is greater than 0.40 m$^2$/g.

10. The oral disintegrating tablet of claim 1, wherein a crystal structure of the D-mannitol is a β-type crystal.

11. The oral disintegrating tablet of claim 1, wherein the binder is at least one material selected from the group consisting of hydroxypropyl cellulose and pregelatinized starch.

12. The oral disintegrating tablet of claim 11, wherein the binder is hydroxypropyl cellulose and a 2% aqueous solution of the hydroxypropyl cellulose has a viscosity of from 2 to 10 mPa·s at 20° C.

13. The oral disintegrating tablet of claim 1, comprising the binder in an amount of from 0.01 to 2% by weight.

14. The oral disintegrating tablet of claim 1, wherein the starch is at least one starch selected from the group consisting of corn starch, potato starch, rice starch, wheat starch, and partially pregelatinized starch.

15. The oral disintegrating tablet of claim 1, wherein the active ingredient is amlodipine or a pharmaceutically acceptable salt thereof.

16. The oral disintegrating tablet of claim 15, wherein the active ingredient is amlodipine besylate.

17. The oral disintegrating tablet of claim 1, wherein the active ingredient is a particle granulated or coated with a coating agent.

18. The oral disintegrating tablet of claim 1, wherein the active ingredient is amlodipine, or a pharmaceutically acceptable salt thereof, granulated or coated with a coating agent.

19. The oral disintegrating tablet of claim 1, wherein the active ingredient is amlodipine besylate granulated or coated with a coating agent.

20. An oral disintegrating tablet, comprising:
(1) particulate D-mannitol having an average particle size of greater than 30 μm and a specific surface area of greater than 0.40 m$^2$/g,
(2) 0.1 to 50% by weight of an active ingredient,
(3) 1 to 10% by weight of crospovidone, carmellose, or a combination thereof,
(4) 2% by weight or less of hydroxypropyl cellulose, a pregelatinized starch, or a combination thereof,
(5) 5 to 20% by weight of a starch, and
(6) 0.1 to 5% by weight of sodium stearyl fumarate,
wherein the tablet disintegrates in an oral cavity within 30 seconds and has an absolute hardness of 2.5 N/mm$^2$ or more.

21. The oral disintegrating tablet of claim 1, comprising the at least one binder in an amount of less than 2% by weight.

* * * * *